United States Patent
Kley et al.

(10) Patent No.: US 10,793,522 B2
(45) Date of Patent: Oct. 6, 2020

(54) SULFONAMIDES AS INHIBITORS OF THE UPTAKE OF EXTRACELLULAR CITRATE

(71) Applicant: Boehringer Ingelheim International GmbH, Ingelheim am Rhein (DE)

(72) Inventors: Joerg Kley, Mittelbiberach (DE); Stefan Kauschke, Biberach an der Riss (DE); Alexander Pautsch, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/467,499

(22) PCT Filed: Dec. 4, 2017

(86) PCT No.: PCT/EP2017/081359
§ 371 (c)(1),
(2) Date: Jun. 7, 2019

(87) PCT Pub. No.: WO2018/104220
PCT Pub. Date: Jun. 14, 2018

(65) Prior Publication Data
US 2020/0062708 A1 Feb. 27, 2020

(30) Foreign Application Priority Data
Dec. 9, 2016 (EP) .................... 16203086

(51) Int. Cl.
*C07D 211/96* (2006.01)
*C07D 401/12* (2006.01)
*C07D 417/12* (2006.01)
*A61K 31/454* (2006.01)
*A61K 31/4545* (2006.01)
*A61K 31/445* (2006.01)

(52) U.S. Cl.
CPC .......... *C07D 211/96* (2013.01); *C07D 401/12* (2013.01); *C07D 417/12* (2013.01)

(58) Field of Classification Search
CPC .. C07D 211/96; C07D 401/12; C07D 417/12; A61P 9/00; A61P 3/00
See application file for complete search history.

(56) References Cited

FOREIGN PATENT DOCUMENTS

| WO | 2010080183 A1 | 7/2010 |
| WO | 2015008872 A1 | 1/2015 |
| WO | 2018104220 A1 | 6/2018 |

OTHER PUBLICATIONS

Schumann, T., "Solute Carrier Transporters as Potential Targets for the Treatment of Metabolic Disease." Pharmacological Reviews 72.1 (2020): 343-379.*
Huard, Optimization of a Dicarboxylic Series for in Vivo inhibition of Citrate Transport by the Solute Carrier 13 Family, J. of medicinal Chem, 2016.
International Search Report for PCT/EP2017/081359 dated Feb. 1, 2018.
Pajor, Sodium-Coupled dicarboxylate and citrate transporters from the SLC13 family, Eur. J. Physiol. 2014, p. 119-130.
Xie, Discovery of potent non-urea inhibitors of soluble epoxise hydrolase, Bioorganic and Medicinal Chem. Letters, 2009, p. 2354-2359.
Written Opinion for PCT.EP2017/081359 dated Feb. 2, 2018.
Brachs, Slc13a5/mINDY inhibition prevents diet-induced non-alcoholic fatty liver disease in mice and rats, Diabetologie und Stoffwechsel, 2016.

* cited by examiner

*Primary Examiner* — John M Mauro
(74) *Attorney, Agent, or Firm* — David L. Kershner

(57) ABSTRACT

The present invention relates to sulfonamides of formula (I)

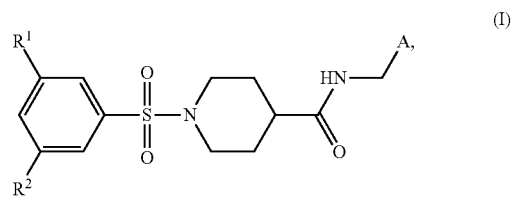

wherein A, $R^1$, and $R^2$ are as defined herein. Also disclosed are medicaments comprising the compounds of formula (I) and their use for the treatment of metabolic and/or cardiovascular diseases.

14 Claims, No Drawings

SULFONAMIDES AS INHIBITORS OF THE UPTAKE OF EXTRACELLULAR CITRATE

FIELD OF THE INVENTION

This invention relates to substituted 1-(benzenesulfonyl)-piperidine-4-carboxylic acid amide derivatives and to their use as inhibitors of the uptake of extracellular citrate, to pharmaceutical compositions containing the same, and to methods of using the same as agents for the treatment of metabolic and/or cardiovascular diseases.

BACKGROUND OF THE INVENTION

As citrate is known to be a key intermediate in energy metabolism, the inhibition of sodium-coupled citrate transporters, such as SLC13A5 (NaCT), predominantly located in the liver and the brain, has attracted interest as a potential therapeutic approach, e.g. for the treatment of metabolic disorders and diseases (Pajor, *Pflugers Arch—Eur J Physiol* 2014, 466, 119-130).

Potent and selective inhibitors of SLC13A5, characterized by a dicarboxylate moiety, are disclosed by Huard et al. (*Sci. Rep.* 2015, 5, 17391; *J. Med. Chem.* 2016, 59, 1165-1175). The same structural motif is shared by the inhibitor reported by Brachs et al. (*Diabetologie und Stoffwechsel* 2016; 11-P163).

Substituted 1-(benzenesulfonyl)-piperidine-4-carboxylic acid amide derivatives have been described as soluble epoxide hydrolase (sEH) inhibitors (Xie et al., *Bioorg. Med. Chem. Lett.* 2009, 19, 2354-2359; WO 2010/080183).

Cyanotriazole compounds as stimulators of the citric acid cycle activity are disclosed in WO 2015/008872.

SUMMARY OF THE INVENTION

In a first aspect, the present invention relates to a compound of formula (I)

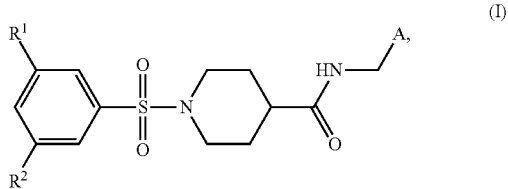

wherein
$R^1$ and $R^2$ are independently selected from the group $R^1$-G1 consisting of halogen, CN, $C_{1-3}$-alkyl and $C_{1-4}$-alkyl-O—;
A is selected from the group A-G1 consisting of
phenyl, substituted with $R^3$ and optionally substituted with $R^4$,
2-pyridyl, optionally substituted with $R^5$,
3-pyridyl, optionally substituted with $R^6$ and
2-thiazolyl, optionally substituted with $R^7$;
wherein $R^3$, $R^4$, $R^5$, $R^6$ and $R^7$ are independently selected from the group $R^1$-G1 as defined hereinbefore;
or a salt thereof.

In a second aspect, the present invention relates to a pharmaceutical composition comprising one or more compounds of formula (I), as defined hereinbefore or hereinafter, or a pharmaceutically acceptable salt thereof and one or more pharmaceutically acceptable excipients.

In a third aspect, the present invention relates to a method for the treatment of one or more metabolic and/or cardiovascular diseases in a patient in need thereof characterized in that a compound of formula (I), as defined hereinbefore or hereinafter, or a pharmaceutically acceptable salt thereof is administered to the patient.

In a further aspect, the present invention relates to a compound of formula (I), as defined hereinbefore or hereinafter, or a pharmaceutically acceptable salt thereof for use in a method for the treatment of one or more metabolic and/or cardiovascular diseases in a patient in need thereof, the method being characterized in that said compound is administered to the patient.

In a further aspect, the present invention relates to the use of a compound of formula (I), as defined hereinbefore or hereinafter, or a pharmaceutically acceptable salt thereof in the manufacture of a medicament for the treatment of one or more metabolic and/or cardiovascular diseases in a patient in need thereof, the method being characterized in that said compound or a pharmaceutically acceptable salt thereof is administered to the patient.

Other aspects of the present invention will become apparent to the person skilled in the art directly from the foregoing and following description.

DETAILED DESCRIPTION OF THE INVENTION

The present invention discloses novel inhibitors of the sodium-coupled citrate transporter SLC13A5 which may be useful in the treatment of diseases and/or conditions associated with or modulated by uptake of extracellular citrate, including but not limited to the treatment of metabolic and/or cardiovascular diseases.

In a first aspect of the present invention, it is found that compounds of formula (I)

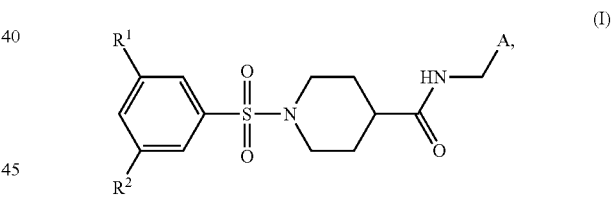

wherein $R^1$, $R^2$ and A are defined as hereinbefore and hereinafter, are potent and selective inhibitors of SLC13A5.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salt" refers to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The term halogen generally denotes fluorine, chlorine, bromine and iodine.

The term "$C_{1-n}$-alkyl", wherein n is an integer, either alone or in combination with another radical, denotes an acyclic, saturated, branched or linear hydrocarbon radical with 1 to n C atoms. For example the term $C_{1-4}$-alkyl embraces the radicals $H_3C$-(Me), $H_3C$—$CH_2$-(Et), $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

In experiments performed on two different cellular systems of citrate uptake, HepG2 cells endogenously expressing human SLC13A5 (hSLC13A5) or HEK293 Flp-In cells over-expressing hSLC13A5, compounds of the invention revealed unexpected inhibitory activity. This effect is thus attributed to the inhibition of SLC13A5 and considered to be relevant under physiological conditions. Also, selectivity of the inhibitory activity within the SLC family of membrane transport proteins could be demonstrated by tests with the glycine transporter 2 (GlyT2, SLC6A5). The results of these investigations are described in more detail in section Examples and Experimental Data.

Therefore, the compounds of formula (I), as defined hereinbefore or hereinafter, or pharmaceutically acceptable salts thereof are expected to be useful in the treatment of diseases and/or conditions associated with or modulated by uptake of extracellular citrate, including but not limited to the treatment of metabolic and/or associated cardiovascular diseases.

Thus, according to one aspect of the present invention, a compound of formula (I)

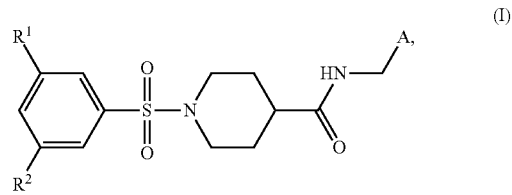

wherein $R^1$, $R^2$ and A are defined as hereinbefore or hereinafter, or a salt thereof is provided.

According to one embodiment, $R^1$ is selected from the group $R^1$-G1 consisting of halogen, CN, $C_{1-3}$-alkyl and $C_{1-4}$-alkyl-O—.

According to another embodiment, $R^1$ is selected from the group $R^1$-G2 consisting of Cl, Br, methyl, methoxy and ethoxy.

According to another embodiment, $R^1$ is selected from the group $R^1$-G3 consisting of Cl, Br and ethoxy.

According to another embodiment, $R^1$ is selected from the group $R^1$-G4 consisting of Cl, Br and methyl.

According to one embodiment, $R^2$ is selected from the group $R^1$-G1 consisting of halogen, CN, $C_{1-3}$-alkyl and $C_{1-4}$-alkyl-O—.

According to another embodiment, $R^2$ is selected from the group $R^2$-G2 consisting of Cl, Br and methyl.

According to another embodiment, $R^2$ is selected from the group $R^2$-G3 consisting of Cl and Br.

According to one embodiment, A is selected from the group A-G1 consisting of phenyl, substituted with $R^3$ and optionally substituted with $R^4$, 2-pyridyl, optionally substituted with $R^5$,
3-pyridyl, optionally substituted with $R^6$ and
2-thiazolyl, optionally substituted with $R^7$,
wherein $R^3$, $R^4$, $R^5$, $R^6$ and $R^7$ are defined as hereinbefore or hereinafter.

According to another embodiment, A is selected from the group A-G2 consisting of phenyl, substituted with $R^3$ and optionally substituted with $R^4$, wherein
$R^3$ and $R^4$ are defined as hereinbefore or hereinafter.

According to another embodiment, A is selected from the group A-G3 consisting of 2-pyridyl, optionally substituted with $R^5$, wherein
$R^5$ is defined as hereinbefore or hereinafter.

According to another embodiment, A is selected from the group A-G4 consisting of 3-pyridyl, optionally substituted with $R^6$, wherein
$R^6$ is defined as hereinbefore or hereinafter.

According to another embodiment, A is selected from the group A-G5 consisting of 2-thiazolyl, optionally substituted with $R^7$, wherein
$R^7$ is defined as hereinbefore or hereinafter.

According to one embodiment, $R^3$ is selected from the group $R^1$-G1 consisting of halogen, CN, $C_{1-3}$-alkyl and $C_{1-4}$-alkyl-O—.

According to another embodiment, $R^3$ is selected from the group $R^3$-G2 consisting of halogen, CN, methyl and methoxy.

According to another embodiment, $R^3$ is selected from the group $R^3$-G3 consisting of F, Cl and CN.

According to one embodiment, $R^4$ is selected from the group $R^1$-G1 consisting of halogen, CN, $C_{1-3}$-alkyl and $C_{1-4}$-alkyl-O—.

According to another embodiment, $R^4$ is selected from the group $R^4$-G2 consisting of F and methyl.

According to another embodiment, $R^4$ is selected from the group $R^4$-G3 consisting of F.

According to one embodiment, $R^5$ is selected from the group $R^1$-G1 consisting of halogen, CN, $C_{1-3}$-alkyl and $C_{1-4}$-alkyl-O—.

According to another embodiment, $R^5$ is selected from the group $R^5$-G2 consisting of halogen, methyl and ethyl.

According to another embodiment, $R^5$ is selected from the group $R^5$-G3 consisting of F and ethyl.

According to one embodiment, $R^6$ is selected from the group $R^1$-G1 consisting of halogen, CN, $C_{1-3}$-alkyl and $C_{1-4}$-alkyl-O—.

According to another embodiment, $R^6$ is selected from the group $R^6$-G2 consisting of Cl, methyl and methoxy.

According to one embodiment, $R^7$ is selected from the group $R^1$-G1 consisting of halogen, CN, $C_{1-3}$-alkyl and $C_{1-4}$-alkyl-O—.

According to another embodiment, $R^7$ is selected from the group $R^7$-G2 consisting of methyl.

According to one embodiment, the compound of formula (I) is selected from the group consisting of (I-5) and (I-10)

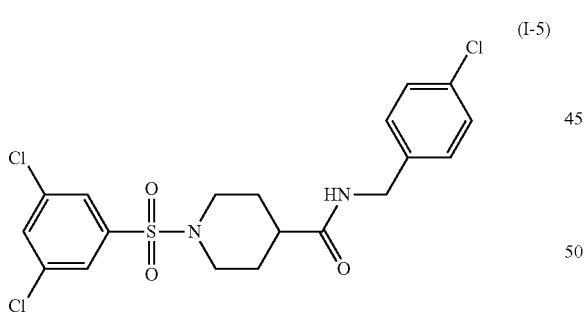

(I-5)

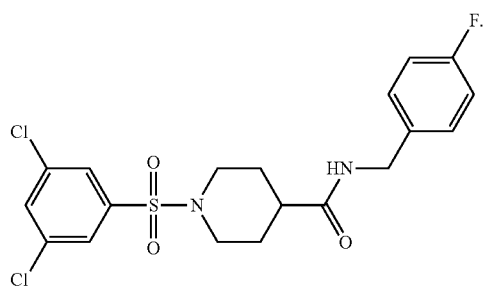

(I-10)

According to another embodiment, the compound of formula (I) is selected from the group consisting of (I-20) and (I-61)

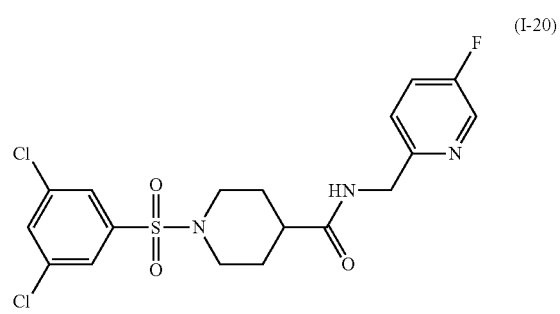

(I-20)

(I-61)

Further preferred subgeneric embodiments of the compounds of formula (I) are set forth as embodiments (I-a) to (I-f) in the following table, wherein the above-mentioned substituent definitions are used and wherein the substituents $R^4$, $R^5$, $R^6$ and $R^7$ are optional (as described in the definition of substituent A), i.e. they may be present or not:

| Embodiment | Substituents | | | | | | | |
| | $R^1$ | $R^2$ | A | $R^3$ | $R^4$ | $R^5$ | $R^6$ | $R^7$ |
| --- | --- | --- | --- | --- | --- | --- | --- | --- |
| (I-a) | $R^1$-G2 | $R^2$-G2 | A-G2 | $R^3$-G2 | $R^4$-G2 | — | — | — |
| (I-b) | $R^1$-G3 | $R^2$-G3 | A-G2 | $R^3$-G3 | $R^4$-G3 | — | — | — |
| (I-c) | $R^1$-G2 | $R^2$-G3 | A-G3 | — | — | $R^5$-G2 | — | — |
| (I-d) | $R^1$-G4 | $R^2$-G3 | A-G3 | — | — | $R^5$-G3 | — | — |
| (I-e) | $R^1$-G3 | $R^2$-G3 | A-G4 | — | — | — | $R^6$-G2 | — |
| (I-f) | $R^1$-G2 | $R^2$-G2 | A-G5 | — | — | — | — | $R^7$-G2 |

The compounds according to the present invention and their intermediates may be obtained using methods of synthesis which are known to the one skilled in the art and described in the literature of organic synthesis. Preferably, the compounds are obtained in analogous fashion to the general and specific methods of preparation explained more fully hereinafter, in particular in section Examples and Experimental Data. In some cases, the order in carrying out the reaction steps may be varied. Variants of the reaction methods that are known to the one skilled in the art, but not described in detail here, may also be used.

The general processes for preparing the compounds according to the invention will become apparent to the one skilled in the art studying the schemes hereinafter. Starting materials may be prepared by methods that are described in the literature or herein, or may be prepared in an analogous or similar manner Any functional groups in the starting materials or intermediates may be protected using conventional protecting groups. These protecting groups may be cleaved again at a suitable stage within the reaction sequence using methods familiar to the one skilled in the art.

by distilling off the solvent under reduced pressure and recrystallizing the residue obtained from a suitable solvent or subjecting it to one of the customary purification methods, such as, for example, column chromatography on a suitable support material.

The compounds according to the present invention are advantageously obtainable using the methods described in section Examples and Experimental Data, which may also be combined for this purpose with methods known to the skilled person from his/her expert knowledge. Likewise, further compounds according to this invention, whose preparations are not explicitly described hereinbefore or hereinafter, can be prepared analogously or similarly to the examples.

The pharmaceutically acceptable salts of the present invention can be synthesized by conventional chemical methods from the parent compound which may contain a basic moiety. Generally, such salts can be prepared by reacting the free base forms of these compounds with a sufficient amount of the appropriate acid in water or in an organic diluent like ether, ethyl acetate, ethanol, isopropa-

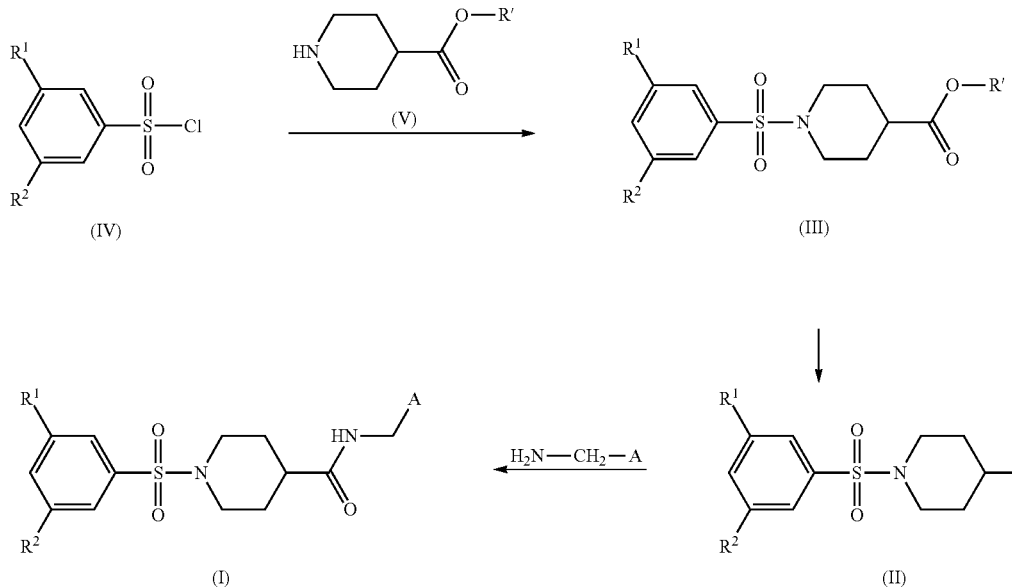

Compounds of formula (I) can be prepared by standard amidation procedures from acids of formula (II) and primary amines of formula H₂N—CH₂-A wherein A is defined as hereinbefore or hereinafter, applying e.g. the coupling reagent HATU in the presence of a base, e.g. DIPEA. Compounds of formula (II) can be prepared by standard deprotection procedures from esters of formula (III). Esters of formula (III) can be prepared from sulfonyl chlorides of formula (IV) and esters of formula (V) (in which R¹ denotes a protecting group, e.g. methyl or ethyl) in the presence of a base, e.g. triethylamine, in a solvent like e.g. dichloromethane.

The substituents R¹, R² and A can be modified by procedures of organic synthesis known to the person skilled in the art. The meaning of the substituents R¹, R² and A prior to such modifications may thereby deviate from the definitions used for compounds of formula (I) hereinbefore or hereinafter.

The compounds according to the present invention are isolated and purified in a manner known per se, for example nol, or acetonitrile, or a mixture thereof. Salts of other acids than those mentioned above which, for example, are useful for purifying or isolating the compounds of the present invention (e.g. trifluoro acetate salts) are also part of the invention.

In a second aspect of the present invention, it is described that a compound of the invention or a pharmaceutically acceptable salt thereof may be used as active ingredients in pharmaceutical compositions.

Suitable preparations for administering the compounds of the invention will be apparent to those with ordinary skill in the art and include for example tablets, pills, capsules, suppositories, lozenges, troches, solutions, syrups, elixirs, sachets, injectables, inhalatives and powders etc.

Suitable tablets may be obtained, for example, by mixing one or more compounds according to formula (I) with known excipients, for example inert diluents, carriers, disintegrants, adjuvants, surfactants, binders and/or lubricants.

In one embodiment, a pharmaceutical composition comprising at least one compound of formula (I), as defined hereinbefore or hereinafter, or a pharmaceutically acceptable salt thereof and at least one pharmaceutically acceptable excipient is provided, preferably as a solid oral dosage form, more preferably selected from the group consisting of coated and uncoated tablets.

In a third aspect of the present invention, the compounds of the invention are useful in methods for the treatment of metabolic and/or cardiovascular diseases, due to their citrate transport inhibitory activity.

Thus, the present invention relates to a compound of formula (I) as defined hereinbefore or hereinafter or a pharmaceutically acceptable salt thereof for use in above-mentioned method of treatment. Also the present invention relates to the use of said compound or of pharmaceutically acceptable salt thereof in the manufacture of a medicament for above-mentioned method of treatment.

In a further aspect, the present invention relates to a method for the treatment of above mentioned diseases and conditions, which method comprises the administration of a compound of general formula (I) to a human being, in particular of a therapeutically effective amount thereof.

The actual therapeutically effective amount or therapeutic dosage will usually depend on factors known by those skilled in the art such as age and weight of the patient, route of administration and severity of disease. In any case, the compounds will be administered at dosages and in a manner which allows a therapeutically effective amount to be delivered based upon patient's unique condition.

According to this aspect of the present invention, a method for the treatment of one or more metabolic and/or cardiovascular diseases in a patient in need thereof is provided characterized in that a therapeutically effective amount of at least one compound of formula (I), as defined hereinbefore or hereinafter, or a pharmaceutically acceptable salt thereof is administered to the patient.

EXAMPLES AND EXPERIMENTAL DATA

The following examples are for the purpose of illustration of the invention only and are not intended in any way to limit the scope of the present invention.

The following abbreviations are used hereinbefore and hereinafter:
ACN Acetonitrile
Aq. aqueous
DCM Dichloromethane
DIPEA Diisopropyl-ethylamine
DMF N,N-Dimethylformamide
ESI Electrospray ionization
h hour
HATU O-(7-Azabenzotriazol-1-yl)-N,N,N',N'-tetramethyl-uronium hexafluorophosphate
min minutes
r.t. ambient temperature (about 20° C.)
RT retention time
TFA Trifluoroacetic acid (1) Chemical Synthesis of Compounds of Formula (IV)

The sulfonyl chlorides applied in the synthesis of example compounds are known in the literature or are prepared according to procedures known in the literature of organic synthesis.

| Intermediate | Structure | Comment |
|---|---|---|
| (IV-1) | 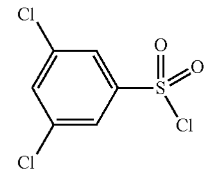 | |
| (IV-2) | 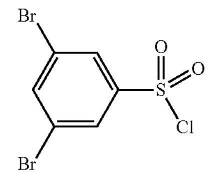 [SMILES: O=S(=O)(Cl)c1cc(Cl)cc(Cl)c1] | |
| (IV-3) | 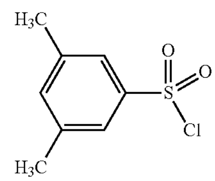 | |
| (IV-4) | 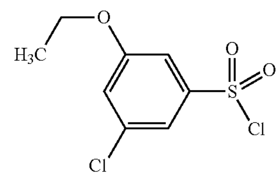 | Prepared analogously to the procedure described for the synthesis of intermediate (IV-5) in WO2008/113760 |
| (IV-5) | 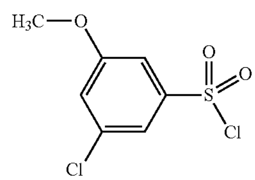 | Synthesis described in WO2008/113760 |
| (IV-6) | 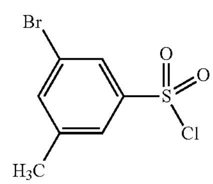 | Synthesis described in WO2009/030715 |

(2) Chemical Synthesis of Compounds of Formula (I)

Example (I-1)

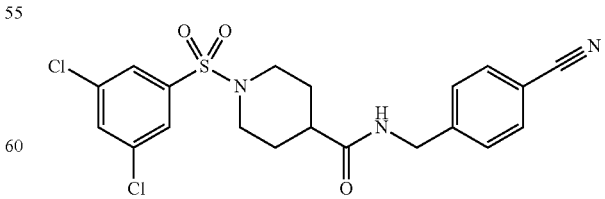

Step 1:
To a mixture of the sulfonyl chloride 3,5-dichlorbenzenesulfonyl chloride (10.0 g; 40.7 mmol) and DCM (100 mL), methyl isonipecotate (6.05 mL; 44.8 mmol) and triethylamine (6.25 mL; 44.8 mmol) are added. The mixture is stirred at r.t. overnight. The mixture is washed successively with aq. HCl (1 mol/L) and water. The organic layer is dried over MgSO$_4$, filtered and the solvent is removed in vacuo.

$C_{13}H_{15}Cl_2NO_4S$ ESI pos.+neg. (Loop-Inj.): [M+H]$^+$352 m/z

HPLC (RT): 1.05 min (HPLC method B)

Step 2:

A mixture of the intermediate obtained from step 1 (14.9 g; 42.3 mmol), aq. sodium hydroxide (4 mol/L; 31.7 mL; 127 mmol) and methanol (100 mL) are stirred at 70° C. for 3 h. After cooling to r.t. the reaction mixture is added to aq. HCl (4 mol/L; 50 mL), the precipitate is filtered off and dried at 50° C.

$C_{12}H_{13}Cl_2NO_4S$ ESI pos.+neg. (Loop-Inj.): [M+H]$^+$338 m/z

HPLC (RT): 0.96 min (HPLC method B)

Step 3:

A mixture of the intermediate obtained from step 2 (1.00 g; 2.96 mmol), HATU (1.24 g; 3.25 mmol), DMF (2.50 mL) and DIPEA (0.56 mL; 3.25 mmol) is stirred at r.t. for 20 min. The amine 4-cyanobenzylamine (0.36 mL, 2.96 mmol) is added and the resulting mixture is stirred at r.t. for 2 h. A molar surplus of aq. NaHCO$_3$ solution is added with stirring and the precipitate is filtered off and dried at 50° C. to yield the title compound.

$C_{20}H_{19}Cl_2N_3O_3S$ ESI pos.+neg. (Loop-Inj.): [M+H]$^+$452 m/z

HPLC (RT): 0.70 min (HPLC method A)

The following example compounds are prepared according to the procedure described for the synthesis of example (I-1) from the respective sulfonyl chloride and the respective amine as indicated in the table.

In cases where the amine is applied as a hydrochloride (or other salt), additional molar equivalents of DIPEA are added in step 3. In cases where the title compound is not readily obtained by precipitation in good quality, it is purified (after extraction with e.g. DCM) by preparative HPLC.

| Example | Structure | Sulfonyl chloride | Amine | [M + H]$^+$ [m/z] | HPLC RT [min] (HPLC method) |
|---|---|---|---|---|---|
| (I-2) | *structure* | (IV-1) | 2-fluorobenzylamine | 445* | 1.00 (C) |
| (I-3) | *structure* | (IV-1) | (6-chloropyridin-3-yl)methanamine | 462* | 0.86 (E) |
| (I-4) | *structure* | (IV-1) | 3,5-dimethylbenzylamine | 455* | 1.01 (E) |
| (I-5) | *structure* | (IV-1) | 4-chlorobenzylamine | 461* | 1.02 (D) |
| (I-6) | *structure* | (IV-1) | 2-bromobenzylamine | 505* | 0.98 (E) |

-continued

| Example | Structure | Sulfonyl chloride | Amine | [M + H]+ [m/z] | HPLC RT [min] (HPLC method) |
|---|---|---|---|---|---|
| (I-7) | 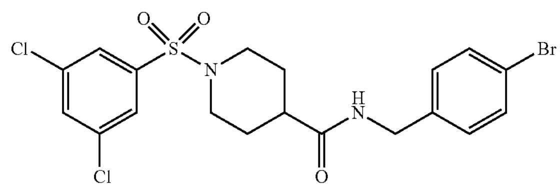 [SMILES: O=C(NCc1ccc(Br)cc1)C1CCN(S(=O)(=O)c2cc(Cl)cc(Cl)c2)CC1] | (IV-1) | | 506* | 1.11 (F) |
| (I-8) | 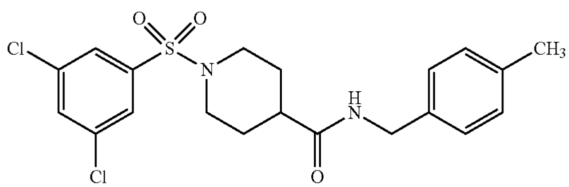 [SMILES: Cc1ccc(CNC(=O)C2CCN(S(=O)(=O)c3cc(Cl)cc(Cl)c3)CC2)cc1] | (IV-1) | | 441* | 0.97 (E) |
| (I-9) | 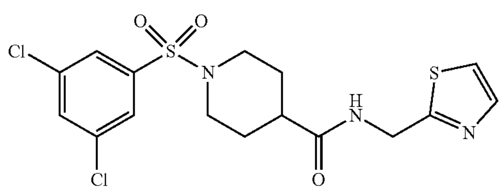 [SMILES: O=C(NCc1nccs1)C1CCN(S(=O)(=O)c2cc(Cl)cc(Cl)c2)CC1] | (IV-1) | | 434** | 0.58 (A) |
| (I-10) | 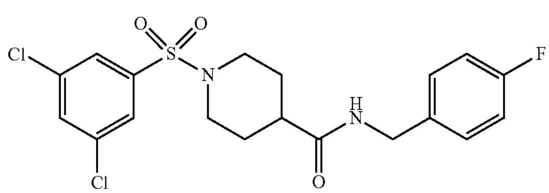 [SMILES: O=C(NCc1ccc(F)cc1)C1CCN(S(=O)(=O)c2cc(Cl)cc(Cl)c2)CC1] | (IV-1) | | 445* | 1.00 (C) |
| (I-11) | 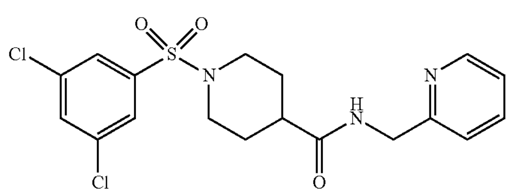 [SMILES: O=C(NCc1ccccn1)C1CCN(S(=O)(=O)c2cc(Cl)cc(Cl)c2)CC1] | (IV-1) | | 428** | 0.51 (A) |
| (I-12) | 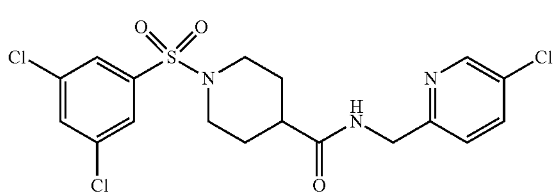 [SMILES: O=C(NCc1ccc(Cl)cn1)C1CCN(S(=O)(=O)c2cc(Cl)cc(Cl)c2)CC1] | (IV-1) | | 462** | 1.09 (B) |
| (I-13) | 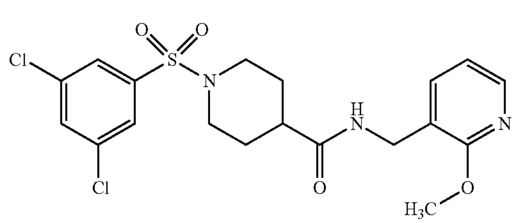 [SMILES: COc1ncccc1CNC(=O)C1CCN(S(=O)(=O)c2cc(Cl)cc(Cl)c2)CC1] | (IV-1) | | 458* | 1.08 (B) |

-continued

| Example | Structure | Sulfonyl chloride | Amine | [M + H]+ [m/z] | HPLC RT [min] (HPLC method) |
|---|---|---|---|---|---|
| (I-14) | 3,5-dichlorophenylsulfonyl-piperidine-4-carboxamide-N-CH2-(4-methylthiazol-2-yl) | (IV-1) | 2-(aminomethyl)-4-methylthiazole | 448* | 0.84 (C) |
| (I-15) | 3,5-dichlorophenylsulfonyl-piperidine-4-carboxamide-N-CH2-(5-methylpyridin-2-yl) | (IV-1) | 2-(aminomethyl)-5-methylpyridine | 442** | 0.89 (B) |
| (I-16) | 3,5-dichlorophenylsulfonyl-piperidine-4-carboxamide-N-CH2-(6-methylpyridin-3-yl) | (IV-1) | 5-(aminomethyl)-2-methylpyridine · 2 HCl | 442** | 0.87 (B) |
| (I-17) | 3,5-dichlorophenylsulfonyl-piperidine-4-carboxamide-N-CH2-(5-ethylpyridin-2-yl) | (IV-1) | 2-(aminomethyl)-5-ethylpyridine [a] | 456** | 0.91 (B) |
| (I-18) | 3,5-dichlorophenylsulfonyl-piperidine-4-carboxamide-N-CH2-(2-chlorophenyl) | (IV-1) | 2-chlorobenzylamine | 461* | 0.97 (E) |
| (I-19) | 3,5-dichlorophenylsulfonyl-piperidine-4-carboxamide-N-CH2-(2-methylphenyl) | (IV-1) | 2-methylbenzylamine | 441* | 0.96 (E) |
| (I-20) | 3,5-dichlorophenylsulfonyl-piperidine-4-carboxamide-N-CH2-(5-fluoropyridin-2-yl) | (IV-1) | 2-(aminomethyl)-5-fluoropyridine | 446** | 0.61 (A) |

-continued

| Example | Structure | Sulfonyl chloride | Amine | [M + H]+ [m/z] | HPLC RT [min] (HPLC method) |
|---|---|---|---|---|---|
| (I-21) | 3,5-dichlorophenylsulfonyl-piperidine-4-carboxamide N-(2-methoxybenzyl) | (IV-1) | 2-methoxybenzylamine | 457* | 1.01 (C) |
| (I-22) | 3,5-dichlorophenylsulfonyl-piperidine-4-carboxamide N-(2-chloro-4-fluorobenzyl) | (IV-1) | 2-chloro-4-fluorobenzylamine | 479* | 0.99 (E) |
| (I-23) | 3,5-dichlorophenylsulfonyl-piperidine-4-carboxamide N-(4-cyano-2-fluorobenzyl) | (IV-1) | 4-cyano-2-fluorobenzylamine ClH | 470** | 1.12 (B) |
| (I-24) | 3,5-dichlorophenylsulfonyl-piperidine-4-carboxamide N-(2,5-difluorobenzyl) | (IV-1) | 2,5-difluorobenzylamine | 463* | 0.94 (E) |
| (I-25) | 3,5-dichlorophenylsulfonyl-piperidine-4-carboxamide N-(4-chloro-2-fluorobenzyl) | (IV-1) | 4-chloro-2-fluorobenzylamine ClH | 479* | 1.00 (E) |
| (I-26) | 3,5-dichlorophenylsulfonyl-piperidine-4-carboxamide N-((6-chloropyridin-2-yl)methyl) | (IV-1) | ClH (6-chloropyridin-2-yl)methanamine | 462* | 0.89 (E) |
| (I-27) | 3,5-dichlorophenylsulfonyl-piperidine-4-carboxamide N-((5-methylthiazol-2-yl)methyl) | (IV-1) | ClH (5-methylthiazol-2-yl)methanamine ClH[b)] | 448** | 1.04 (B) |

-continued

| Example | Structure | Sulfonyl chloride | Amine | [M + H]+ [m/z] | HPLC RT [min] (HPLC method) |
|---|---|---|---|---|---|
| (I-28) | 3,5-dichlorophenylsulfonyl-piperidine-4-carboxamide-N-CH2-(5-bromopyridin-2-yl) | (IV-1) | H2N-CH2-(5-bromopyridin-2-yl) | 506** | 1.10 (B) |
| (I-29) | 3,5-dibromophenylsulfonyl-piperidine-4-carboxamide-N-CH2-(4-methylthiazol-2-yl) | (IV-2) | H2N-CH2-(4-methylthiazol-2-yl) | 536* | 0.87 (C) |
| (I-30) | 3,5-dibromophenylsulfonyl-piperidine-4-carboxamide-N-CH2-(4-chlorophenyl) | (IV-2) | H2N-CH2-(4-chlorophenyl) | 550* | 1.08 (C) |
| (I-31) | 3,5-dibromophenylsulfonyl-piperidine-4-carboxamide-N-CH2-(5-ethylpyridin-2-yl) | (IV-2) | H2N-CH2-(5-ethylpyridin-2-yl) | 544**[a] | 0.93 (B) |
| (I-32) | 3,5-dibromophenylsulfonyl-piperidine-4-carboxamide-N-CH2-(4-cyanophenyl) | (IV-2) | H2N-CH2-(4-cyanophenyl) | 541* | 0.98 (C) |
| (I-33) | 3,5-dibromophenylsulfonyl-piperidine-4-carboxamide-N-CH2-(2-methoxypyridin-3-yl) | (IV-2) | H2N-CH2-(2-methoxypyridin-3-yl) | 546** | 1.12 (B) |
| (I-34) | 3,5-dibromophenylsulfonyl-piperidine-4-carboxamide-N-CH2-(2-methoxyphenyl) | (IV-2) | H2N-CH2-(2-methoxyphenyl) | 545* | 1.04 (C) |

-continued

| Example | Structure | Sulfonyl chloride | Amine | [M + H]+ [m/z] | HPLC RT [min] (HPLC method) |
|---|---|---|---|---|---|
| (I-35) | 3,5-dibromophenylsulfonyl-piperidine-4-carboxamide N-((5-fluoropyridin-2-yl)methyl) | (IV-2) | (5-fluoropyridin-2-yl)methanamine | 534** | 1.08 (B) |
| (I-36) | 3,5-dibromophenylsulfonyl-piperidine-4-carboxamide N-(pyridin-3-ylmethyl) | (IV-2) | pyridin-3-ylmethanamine | 516** | 0.89 (B) |
| (I-37) | 3,5-dibromophenylsulfonyl-piperidine-4-carboxamide N-(pyridin-2-ylmethyl) | (IV-2) | pyridin-2-ylmethanamine | 516** | 0.90 (B) |
| (I-38) | 3,5-dibromophenylsulfonyl-piperidine-4-carboxamide N-(2-fluorobenzyl) | (IV-2) | (2-fluorophenyl)methanamine | 533* | 1.03 (C) |
| (I-39) | 3,5-dibromophenylsulfonyl-piperidine-4-carboxamide N-(4-bromobenzyl) | (IV-2) | (4-bromophenyl)methanamine | 594* | 1.09 (C) |
| (I-40) | 3,5-dibromophenylsulfonyl-piperidine-4-carboxamide N-(4-fluorobenzyl) | (IV-2) | (4-fluorophenyl)methanamine | 533* | 1.03 (C) |
| (I-41) | 3,5-dimethylphenylsulfonyl-piperidine-4-carboxamide N-((4-methylthiazol-2-yl)methyl) | (IV-3) | (4-methylthiazol-2-yl)methanamine | 408* | 0.77 (C) |

-continued

| Example | Structure | Sulfonyl chloride | Amine | [M + H]+ [m/z] | HPLC RT [min] (HPLC method) |
|---|---|---|---|---|---|
| (I-42) | 3,5-dimethylphenylsulfonyl-piperidine-4-carboxamide N-(4-fluorobenzyl) | (IV-3) | 4-fluorobenzylamine | 405* | 0.94 (C) |
| (I-43) | 3,5-dimethylphenylsulfonyl-piperidine-4-carboxamide N-(4-cyanobenzyl) | (IV-3) | 4-cyanobenzylamine | 412* | 0.89 (C) |
| (I-44) | 3,5-dimethylphenylsulfonyl-piperidine-4-carboxamide N-(2-methoxybenzyl) | (IV-3) | 2-methoxybenzylamine | 417* | 0.95 (C) |
| (I-45) | 3,5-dimethylphenylsulfonyl-piperidine-4-carboxamide N-(4-chlorobenzyl) | (IV-3) | 4-chlorobenzylamine | 421* | 0.99 (C) |
| (I-46) | 3,5-dimethylphenylsulfonyl-piperidine-4-carboxamide N-((5-methylthiazol-2-yl)methyl) | (IV-3) | (5-methylthiazol-2-yl)methanamine · ClH [b)] | 408** | 0.62 (A) |
| (I-47) | 3,5-dimethylphenylsulfonyl-piperidine-4-carboxamide N-(2-fluorobenzyl) | (IV-3) | 2-fluorobenzylamine | 405* | 0.95 (C) |
| (I-48) | 3,5-dimethylphenylsulfonyl-piperidine-4-carboxamide N-(4-bromobenzyl) | (IV-3) | 4-bromobenzylamine | 465* | 1.00 (C) |

-continued

| Example | Structure | Sulfonyl chloride | Amine | [M + H]+ [m/z] | HPLC RT [min] (HPLC method) |
|---|---|---|---|---|---|
| (I-49) | H3C-O-C6H3(Cl)-SO2-N(piperidine)-C(O)-NH-CH2-thiazole | (IV-4) | thiazol-2-yl-CH2-NH2·HCl | 444** | 1.04 (B) |
| (I-50) | H3C-O-C6H3(Cl)-SO2-N(piperidine)-C(O)-NH-CH2-C6H3(F)(CN) | (IV-4) | H2N-CH2-C6H3(F)(CN)·HCl | 480** | 1.14 (B) |
| (I-51) | H3C-O-C6H3(Cl)-SO2-N(piperidine)-C(O)-NH-CH2-C6H4-F | (IV-4) | H2N-CH2-C6H4-F | 455** | 1.16 (B) |
| (I-52) | H3C-O-C6H3(Cl)-SO2-N(piperidine)-C(O)-NH-CH2-(5-Cl-pyridin-2-yl) | (IV-4) | (5-Cl-pyridin-2-yl)-CH2-NH2·2HCl | 472** | 1.12 (B) |
| (I-53) | H3C-O-C6H3(Cl)-SO2-N(piperidine)-C(O)-NH-CH2-(pyridin-2-yl) | (IV-4) | H2N-CH2-(pyridin-2-yl) | 438** | 0.88 (B) |
| (I-54) | H3C-O-C6H3(Cl)-SO2-N(piperidine)-C(O)-NH-CH2-C6H4-CN | (IV-4) | H2N-CH2-C6H4-CN | 462** | 1.11 (B) |
| (I-55) | H3C-O-C6H3(Cl)-SO2-N(piperidine)-C(O)-NH-CH2-(5-F-pyridin-2-yl) | (IV-4) | H2N-CH2-(5-F-pyridin-2-yl) | 456** | 1.07 (B) |
| (I-56) | H3C-O-C6H3(Cl)-SO2-N(piperidine)-C(O)-NH-CH2-(5-F-pyridin-2-yl) | (IV-5) | H2N-CH2-(5-F-pyridin-2-yl) | 442** | 1.02 (B) |

-continued

| Example | Structure | Sulfonyl chloride | Amine | [M + H]+ [m/z] | HPLC RT [min] (HPLC method) |
|---|---|---|---|---|---|
| (I-57) | 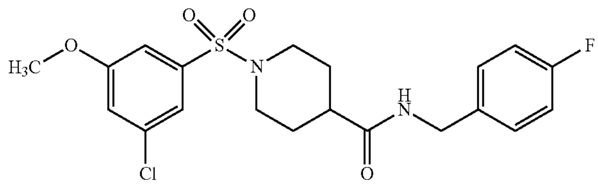 [SMILES: COc1cc(Cl)cc(S(=O)(=O)N2CCC(C(=O)NCc3ccc(F)cc3)CC2)c1] | (IV-5) | | 441** | 1.11 (B) |
| (I-58) | 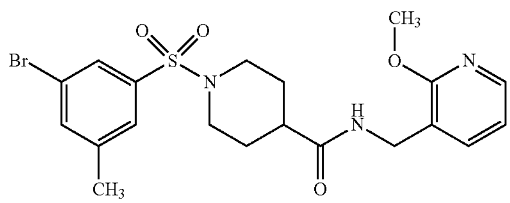 [SMILES: COc1ncccc1CNC(=O)C1CCN(S(=O)(=O)c2cc(C)cc(Br)c2)CC1] | (IV-6) | | 482** | 1.08 (B) |
| (I-59) | 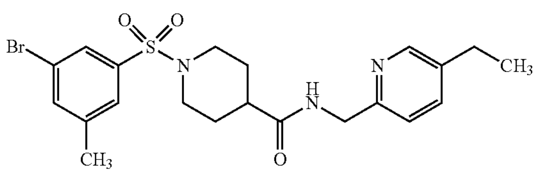 [SMILES: CCc1ccc(CNC(=O)C2CCN(S(=O)(=O)c3cc(C)cc(Br)c3)CC2)nc1] | (IV-6) | | 480** | 0.86 (B) |
| (I-60) | 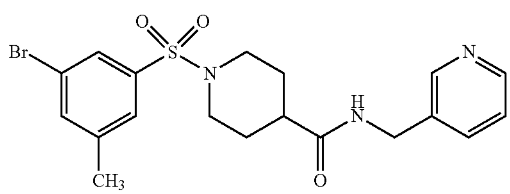 [SMILES: Cc1cc(Br)cc(S(=O)(=O)N2CCC(C(=O)NCc3cccnc3)CC2)c1] | (IV-6) | | 452** | 0.85 (B) |
| (I-61) | 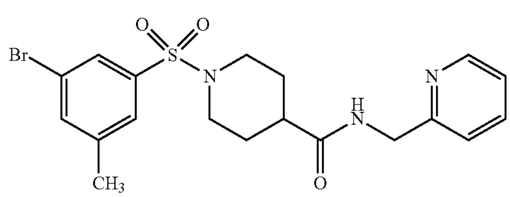 [SMILES: Cc1cc(Br)cc(S(=O)(=O)N2CCC(C(=O)NCc3ccccn3)CC2)c1] | (IV-6) | | 452** | 0.86 (B) |
| (I-62) | 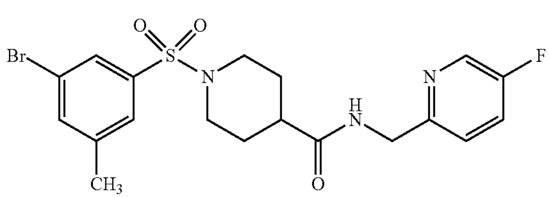 [SMILES: Cc1cc(Br)cc(S(=O)(=O)N2CCC(C(=O)NCc3ccc(F)cn3)CC2)c1] | (IV-6) | | 470** | 1.04 (B) |

*generated with ESI-MS [M + H]+

**generated with ESI pos. + neg. (Loop-Inj.) [M + H]+

[a] 2-Aminomethyl-5-ethylpyridine is prepared from 2-cyano-5-ethylpyridine analogously to the procedure described for the synthesis of 2-aminomethyl-5-methylpyridine from 2-cyano-5-methylpyridine in WO2013/30138.

[b] 2-Aminomethyl-5-methylthiazole is prepared from 2-hydroxymethyl-5-methylthiazole analogously to the sequence described for the synthesis of 2-aminomethyl-4-methylthiazole from 2-hydroxymethyl-4-methylthiazole in WO2009/15369.

(3) Analytical Methods and Preparative Chromatography

As a rule, $^1$H-NMR and mass spectra have been obtained for the compounds prepared. Mass peaks given (e.g. [M+H]$^+$) refer to monoisotopic molecular weight.

Preparative HPLC:

Stationary phase: XBridge™ C18; 10 μm or SunFire™ C18; 10 μm (both from Waters)

Analytical HPLC/MS Methods

The HPLC retention times given are measured under the following parameters.

HPLC Method A

Column: SunFire™ C18, 2.1 × 30 mm, 2.5 μm (Waters)

| Gradient time [min] | % Solvent [H$_2$O, 0.1% TFA] | % Solvent [ACN] | Flow [mL/min] | Temperature [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

HPLC Method B

Column: SunFire™ C18, 3.0 × 30 mm, 2.5 μm (Waters)

| Gradient time [min] | % Solvent [H$_2$O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

HPLC Method C

Column: SunFire™ C18, 3.0 × 30 mm, 2.5 μm (Waters)

| Gradient time [min] | % Solvent [H$_2$O, 0.1% TFA] | % Solvent [ACN, 0.08% TFA] | Flow [mL/min] | Temperature [° C.] |
|---|---|---|---|---|
| 0.0 | 95 | 5 | 1.5 | 60 |
| 1.3 | 0 | 100 | 1.5 | 60 |
| 1.5 | 0 | 100 | 1.5 | 60 |
| 1.6 | 95 | 5 | 1.5 | 60 |

HPLC Method D

Column: XBridge™ C18, 3.0 × 30 mm, 2.5 μm (Waters)

| Gradient time [min] | % Solvent [H$_2$O, 0.1% NH$_3$] | % Solvent [ACN] | Flow [mL/min] | Temperature [° C.] |
|---|---|---|---|---|
| 0.0 | 95 | 5 | 1.5 | 60 |
| 1.3 | 1.0 | 99 | 1.5 | 60 |
| 1.5 | 0.1 | 99.9 | 1.5 | 60 |
| 1.6 | 95 | 5 | 1.5 | 60 |

HPLC Method E

Column: SunFire™ C18, 3.0 × 30 mm, 2.5 μm (Waters)

| Gradient time [min] | % Solvent [H$_2$O, 0.1% TFA] | % Solvent [ACN] | Flow [ml/min] | Temperature [° C.] |
|---|---|---|---|---|
| 0.0 | 98.0 | 2.0 | 2.0 | 60 |
| 1.2 | 0.0 | 100.0 | 2.0 | 60 |
| 1.4 | 0.0 | 100.0 | 2.0 | 60 |

HPLC Method F

Column: XBridge™ C18, 3.0 × 30 mm, 2.5 μm (Waters)

| Gradient time [min] | % Solvent [H$_2$O, 0.1% NH$_3$] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

(4) HepG2/$^{14}$C-Citrate Uptake Assay

HepG2 cells endogenously expressing hSLC13A5 were obtained from the Wistar Institute (Knowles et al., *Science* 1980, 209, 497-499).

Principle:

HepG2 cells endogenously express hSLC13A5 transporter which is responsible for the uptake of citrate into these cells. Uptake of $^{14}$C-citrate can be completely blocked by specific SLC13A5 inhibitors and the signal can be competed with unlabelled citrate. The uptake of $^{14}$C-citrate into HepG2 cells is monitored using the Cytostar-T assay. This assay format is based on the imported radioactive citrate brought into proximity with the scintillant contained within the base of the plate by virtue of the biological processes within the cells. The radioactive decay is converted to a light signal based on the integration of the scintillation matrix into the assay plate.

Method: $^{14}$C-Citrate Uptake Assay

Test Compound Dilutions:

Starting from 10 mM stock solutions in 100% DMSO, compounds are diluted in pure DMSO using the appropriate dilution steps. Prior to the uptake assay, 400 μL assay medium+4.8 μL compound solution (or pure DMSO for non-inhibited control wells) are mixed (final DMSO concentration in the assay: 1% (v/v)) $^{14}$C-citrate working solution (volumes required per 96-well):

1.88 mL assay medium (50% DMEM+50% Ham's F-12+15 mM HEPES (pH7.4) (medium contains 15.5 mM D(+)-glucose)+21.2 μL $^{14}$C-citric acid stock solution (stock: 0.1 mCi/mL=111,000,000 dpm/500 μL; ~1 mmol/L).

The HepG2 cells are cultivated in cell culture medium (EMEM+10% fetal calf serum+1×NEAA and 10 mM L-Glutamin) For the assay, the medium of the confluent cultures is discarded and the cells are washed with DPBS w/o Mg$^{2+}$ w/o Ca$^{2+}$. The cells are detached by the addition of 1.0 mL 2× Trypsin in DPBS w/o Mg$^{2+}$ w/o Ca$^{2+}$ with 7.5 mM EDTA per 75 cm$^2$ culture flask for up to 3 minutes at 37° C. and resuspended in 10 mL cell culture medium. Following cell counting, 100,000 cells/well are seeded in a volume of 200 μL into Cytostar-T Scintillating 96-well microplates. After overnight incubation in a humid cell culture incubator at 37° C., 5% $CO_2$, the cell culture medium is carefully aspirated and the cells are incubated with 200 μL prewarmed (37° C.) assay medium (50% DMEM+50% Ham's F-12+15 mM HEPES (pH 7.4) (medium contains 15.5 m M D(+)-glucose) per well for at least 1 h prior to the experiment.

Immediately prior to uptake assay, the assay medium is carefully removed and 100 μL test compound dilution is added to each well (n=3).

Following a 20 min incubation at 37° C. in the cell culture incubator, 20 μL of $^{14}C$-citrate working solution is added to each well (final volume per well: 120 μL; final $^{14}C$-citrate concentration ~1.8 μM/well)).

After incubation over night at 37° C. in the cell culture incubator, the plates are sealed on the top using a transparent plastic foil and on the bottom using a white plastic foil. Following the sealing, the plate is placed into the TopCount NXT HTS and the signal is recorded.

The $IC_{50}$ values of the compounds are calculated in IDBS XLfit by sigmoidal dose-response (variable slope).

(5) Recombinant hSLC13A5/$^{14}C$-Citrate Uptake Assay

The human embryonic kidney 293 (HEK 293)-Flp-In cells (293Flp-In-hSLC13A5) over-expressing hSLC13A5 transporter were cloned: The originating plasmid pcDNA3.1-hSLC13A5 containing hSLC13A5 was synthesized at GeneArt. The cDNA for hSLC13A5 was taken from this plasmid by means of PCR amplification using primers with added HindIII (N-terminal) and XhoI (C-terminal) restriction sites and sub-cloned in frame into pcDNA5/FRT from Invitrogen using the respective restriction enzymes. HEK293 Flp-In cells from Invitrogen were stably co-transfected using the pcDNA/FRT-hSLC13A5 plasmid as well as the pOG44 plasmid.

Principle:

HEK 293-Flp-In cells are used that stably over-express hSLC13A5 transporter which is responsible for the uptake of citrate into these cells. Uptake of $^{14}C$-citrate can be completely blocked by specific SLC13A5 inhibitors and the signal can be competed with unlabelled citrate.

The uptake of $^{14}C$-citrate into the 293Flp-In-hSLC13A5 cells is monitored using the WGA-PVT SPA (wheat germ agglutinin-polyvinyltoluene scintillation proximity assay) beads that bind to the 293Flp-In cells due to their WGA-PVT surface. This assay format is based on the imported radioactive citrate brought into proximity with the SPA beads by virtue of the biological processes within the cells. The radioactive decay is converted into a light signal that can be measured using e.g. the TopCount plate reader.

Method: $^{14}C$-Citrate Uptake Assay

Test Compound Dilutions (2Fold-Concentrated):

Starting from 10 mM stock solutions in 100% DMSO, compounds are diluted in pure DMSO using the appropriate dilution steps.

Prior to the uptake assay, 200 μL assay medium (lx HBSS (with $Ca^{2+}$ and $Mg^{2+}$, w/o Phenolred), contains 5.56 mM D(+)-Glucose)+19.44 mM D(+)-Glucose (final concentration of D(+)-Glucose is 25 mM))+4.8 μL compound solution (or pure DMSO for non-inhibited control wells) are mixed (final DMSO concentration in the assay: 1% (v/v)).

After preparing the 2fold-concentrated test compound dilutions, 50 μL are pipetted to each well of white Opti-Plates-96 and incubated at 37° C. in an incubator.

$^{14}C$-Citrate Working Solution (Volumes Required Per 96-Well):

2.1 mL assay medium+23.65 μL $^{14}C$-citric acid stock solution (stock: 0.1 mCi/mL=111,000,000 dpm/500 μL).

The 293Flp-In-hSLC13A5 cells are cultivated in cell culture medium (DMEM+10% fetal calf serum+100 μg/mL Hygromycin B). The medium of the confluent cultures is discarded and the cells are washed with DPBS (w/o $Mg^{2+}$ w/o $Ca^{2+}$). The cells are detached by the addition of 2.0 mL Accumax per 75 $cm^2$ culture flask for up to 3 minutes at 37° C. and resuspended in 10 mL assay medium. After cell counting, 50,000 cells/well are administered in a volume of 50 μL into the white OptiPlates-96 containing the respective test compound concentrations. Following a 20 min incubation at 37° C. in the cell culture incubator, 20 μL of $^{14}C$-citrate working solution is added to each well (final volume per well: 120 μL; final $^{14}C$-citrate concentration: approx. 2 μM/well).

After incubation for 4 h at 37° C. in a humid cell culture incubator and the addition of 30 μL of WGA-PVT SPA beads to each well (0.25 mg/well), the plates are sealed on the top using a transparent plastic foil. Incubate the plates for 1 h by room temperature and gentle shaking.

After incubation, the plate is placed into the TopCount NXT HTS and the signal is recorded.

The performance of the test compounds is calculated as follows:

Wells containing cells incubated with 1% DMSO only deliver values for the non-inhibited $^{14}C$-citrate uptake into 293Flp-In-hSLC13A5 cells (100% CTL). Wells containing cells which have received 30 mM non-labelled potassium citrate solution in addition to the $^{14}C$-citrate working solution deliver values for the background (0% CTL).

The $IC_{50}$ values of the compounds are calculated in IDBS XLfit by sigmoidal dose-response (variable slope).

(6) Recombinant Human GlyT2/$^3H$-Glycine Uptake Assay

The human embryonic kidney 293 cell clone (HEK293-hGlyT2) over-expressing the human GlyT2 transporter was generated (the plasmid pCMV6-XL5-hGlyT2 containing the cDNA coding for the human GlyT2 transporter was obtained from Origene, the cDNA for GlyT2 was taken from this plasmid and sub-cloned into pcDNA3.1zeo from Invitrogen).

Principle:

Human embryonic kidney 293 (HEK 293) cells are used that stably over-express the human GlyT2 receptor which is responsible for the uptake of glycine into these cells. Uptake of $^3H$-glycine can be completely blocked by specific GlyT2 inhibitors and the signal can be competed with unlabelled glycine.

The uptake of $^3H$-glycine into the HEK 293 hGlyT2 cells is monitored using the Cytostar-T assay. This assay format is based on the imported radioactive glycine brought into proximity with the scintillant contained within the base of the plate by virtue of the biological processes within the cells. The radioactive decay is converted to a light signal based on the integration of the scintillation matrix into the assay plate.

Method: $^3H$-Glycine Uptake Assay

The hGlyT2 over-expressing HEK 293 cells are cultivated in cell culture medium (DMEM+10% fetal calf serum+100 μg/mL Zeocin). For the assay, the medium of the 90% confluent cultures is removed and the cells are washed with DPBS. The cells are detached by the addition of 2 mL AccuMax and resuspended in 10 mL culture medium. The cell suspension is centrifuged at 1000 U/min for 5 min, the supernatant is removed and cells resuspended in expression medium (MEM (medium without glycine)+10% fetal calf serum) without glycine to 200,000 cells/mL and distributed into the Cytostar-T Scintillating 96-well Microplates (40,000 cells/well; 200 µl/well). The lid covered MTPs are then incubated for 24 hours at 37° C.; 5% $CO_2$.

The following day, the cell plates are washed once with 200 µL HBSS/Ala buffer (HBSS 10× (+Ca, +Mg) with 5 mM Alanine adjusted to pH 7.4 with NaOH) following a 1 h incubation at 37° C.; 5% $CO_2$, and subsequently 100 µL/well of HBSS/Ala containing 1.2× the concentration of compound in 1.2% DMSO (test range final: 100 µM-100 nM) incubated for 20 min at 37° C. Following the addition of 20 µL/well $^3$H-glycine in HBSS/Ala (final $^3$H-glycine concentration 100 nM) and an incubation for 2 hours at 37° C., the assay plate is placed into the Topcount NXT HTS and the signal is recorded.

The $IC_{50}$ values of the compounds are calculated in IDBS XLfit by sigmoidal dose-response (variable slope).

(7) Assay Results for Exemplary Compounds

| Example | HepG2/ $^{14}$C-citrate uptake assay $IC_{50}$ [µM] | Recombinant hSLC13A5/ $^{14}$C-citrate uptake assay $IC_{50}$ [µM] | Recombinant human GlyT2/$^3$H-glycine uptake assay $IC_{50}$ [µM] |
|---|---|---|---|
| (I-1) | 0.074 | 0.079 | >100 |
| (I-2) | 0.035 | 0.087 | >100 |
| (I-3) | 0.471 | | |
| (I-4) | 0.094 | | |
| (I-5) | 0.022 | 0.056 | >100 |
| (I-6) | 0.082 | | |
| (I-7) | 0.030 | | |
| (I-8) | 0.037 | | |
| (I-9) | 0.246 | 0.303 | |
| (I-10) | 0.024 | 0.056 | >100 |
| (I-11) | 0.455 | 0.687 | >100 |
| (I-12) | 0.103 | 0.132 | |
| (I-13) | 0.201 | 0.475 | |
| (I-14) | 0.083 | | |
| (I-15) | 0.152 | 0.193 | >100 |
| (I-16) | 0.632 | 0.675 | |
| (I-17) | 0.130 | 0.138 | |
| (I-18) | 0.060 | | |
| (I-19) | 0.072 | | |
| (I-20) | 0.233 | 0.392 | >70 |
| (I-21) | 0.065 | | |
| (I-22) | 0.084 | | |
| (I-23) | 0.142 | 0.091 | |
| (I-24) | 0.083 | | |
| (I-25) | 0.037 | | |
| (I-26) | 0.290 | 0.449 | |
| (I-27) | 0.113 | 0.341 | >100 |
| (I-28) | 0.171 | 0.127 | |
| (I-29) | 0.043 | | |
| (I-30) | 0.014 | | |
| (I-31) | 0.066 | 0.041 | |
| (I-32) | 0.023 | | |
| (I-33) | 0.182 | 0.275 | |
| (I-34) | 0.027 | | |
| (I-35) | 0.147 | 0.054 | |
| (I-36) | 0.448 | 0.354 | |
| (I-37) | 0.253 | 0.089 | |
| (I-38) | 0.014 | | |
| (I-39) | 0.014 | | |
| (I-40) | 0.017 | 0.026 | |
| (I-41) | 0.155 | 0.438 | |
| (I-42) | 0.035 | | |
| (I-43) | 0.046 | | |
| (I-44) | 0.132 | 0.703 | |
| (I-45) | 0.025 | | |
| (I-46) | 0.202 | 0.398 | |
| (I-47) | 0.034 | | |
| (I-48) | 0.017 | | |
| (I-49) | 0.100 | 0.154 | >100 |
| (I-50) | 0.073 | 0.127 | |
| (I-51) | 0.014 | 0.066 | |
| (I-52) | 0.051 | 0.200 | |
| (I-53) | 0.110 | 0.410 | |
| (I-54) | 0.062 | 0.231 | |
| (I-55) | 0.056 | 0.189 | |
| (I-56) | 0.292 | 0.436 | |
| (I-57) | 0.048 | 0.167 | |
| (I-58) | 0.168 | 0.837 | |
| (I-59) | 0.027 | 0.098 | |
| (I-60) | 0.422 | 0.918 | |
| (I-61) | 0.149 | 0.437 | >100 |
| (I-62) | 0.099 | 0.232 | |

The invention claimed is:

1. A compound of formula (I)

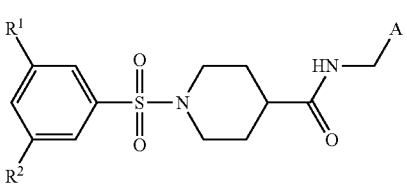

wherein $R^1$ and $R^2$ are independently selected from the group consisting of halogen, CN, $C_{1-3}$-alkyl and $C_{1-4}$-alkyl-O—;

A is selected from the group consisting of phenyl, substituted with $R^3$ and optionally substituted with $R^4$, 2-pyridyl, optionally substituted with $R^5$, 3-pyridyl, optionally substituted with $R^6$ and 2-thiazolyl, optionally substituted with $R^7$;

and wherein $R^3$, $R^4$, $R^5$, $R^6$ and $R^7$ are independently selected from the group consisting of halogen, CN, $C_{1-3}$-alkyl and $C_{1-4}$-alkyl-O— or a salt thereof.

2. The compound according to claim 1 wherein $R^1$ is selected from the group consisting of Cl, Br, methyl, methoxy and ethoxy.

3. The compound according to claim 1 wherein $R^2$ is selected from the group consisting of Cl, Br and methyl.

4. The compound according to claim 1 wherein A is selected from the group consisting of phenyl, substituted with $R^3$ and optionally substituted with $R^4$.

5. The compound according to claim 1 wherein A is selected from the group consisting of 2-pyridyl, optionally substituted with $R^5$.

6. The compound according to claim 1 wherein A is selected from the group consisting of 3-pyridyl, optionally substituted with $R^6$.

7. The compound according to claim 1 wherein A is selected from the group consisting of 2-thiazolyl, optionally substituted with $R^7$.

8. The compound according to claim 1 wherein $R^3$ is selected from the group consisting of halogen, CN, methyl and methoxy.

9. The compound according to claim 1 wherein $R^4$ is selected from the group consisting of F and methyl.

10. The compound according to claim 1 wherein $R^5$ is selected from the group consisting of halogen, methyl and ethyl.

11. The compound according to claim 1 wherein $R^6$ is selected from the group consisting of Cl, methyl and methoxy.

12. The compound according to claim 1 wherein $R^7$ is methyl.

13. A pharmaceutical composition comprising at least one compound of formula (I) according to claim 1 or a pharmaceutically acceptable salt thereof and at least one pharmaceutically acceptable excipient.

14. A method for the treatment of one or more metabolic diseases in a patient in need thereof characterized in that a compound of formula (I) according claim 1 or a pharmaceutically acceptable salt thereof is administered to the patient.

* * * * *